United States Patent [19]
Fuchs et al.

[11] Patent Number: 5,788,646
[45] Date of Patent: Aug. 4, 1998

[54] CENTRAL STATION WAVEFORM DISPLAY HAVING DEDICATED MESSAGE USER AREAS

[75] Inventors: Kenneth Fuchs, Wayland; Brenda L. Yocum, Ipswich; Carolyn Holbrook, Bolton, all of Mass.

[73] Assignee: Siemens Medical Systems, Inc., Iselin, N.J.

[21] Appl. No.: 895,079

[22] Filed: Jul. 16, 1997

Related U.S. Application Data

[63] Continuation of Ser. No. 618,156, Mar. 19, 1996, abandoned.

[51] Int. Cl.$^6$ .................................................. A61B 5/044
[52] U.S. Cl. ............................................................ 600/523
[58] Field of Search ..................................... 600/523, 508, 600/509, 525, 518

[56] References Cited

U.S. PATENT DOCUMENTS

| | | | |
|---|---|---|---|
| 3,909,792 | 9/1975 | Harris et al. | 340/172.5 |
| 4,974,162 | 11/1990 | Siegel et al. | 364/413.06 |
| 5,038,800 | 8/1991 | Oba | 128/904 |
| 5,182,796 | 1/1993 | Shibayama et al. | 395/156 |
| 5,262,944 | 11/1993 | Weisner et al. | 128/712 |
| 5,284,152 | 2/1994 | Portnuff et al. | 128/710 |
| 5,485,567 | 1/1996 | Banning et al. | 395/148 |

FOREIGN PATENT DOCUMENTS

| | | |
|---|---|---|
| 0 269 907 | 6/1988 | European Pat. Off. . |
| 0 386 314 | 9/1990 | European Pat. Off. . |
| WO 90 15380 | 12/1990 | WIPO . |
| WO 95 20794 | 8/1995 | WIPO . |

OTHER PUBLICATIONS

"Patient Monitoring Enhanced By New Central Station", Blancke et al., Hewlett–Packard Journal Nov. 1980, pp. 3–11.

IBM Technical Disclosure Bulletin, "Technique for Annotating a Document Page", vol. 34, No. 10b, Mar. 1992, pp. 53–54.

IBM Technical Disclosure Bulletin, "Quicknote Function to Add Short Notes to a Display", vol. 33, No. 8, Jan. 1991, pp. 258–259.

*Primary Examiner*—Scott M. Getzow
*Attorney, Agent, or Firm*—Lawrence C. Edelman

[57] ABSTRACT

A method and apparatus for displaying physiological signals acquired from a patient in a manner that allows for reliably associating with the physiological signals acquired from the patient user generated message information. The method comprises the steps of, receiving at a central station physiological signals acquired from a patient; and arranging a display portion of the central station to have at least one first display area dedicated for displaying said physiological signals, and at least one second display area, located adjacent said first display area, dedicated for displaying a user generated message related to the physiological signals displayed in said first area.

9 Claims, 4 Drawing Sheets

| VIEW SETUP BIOMED DEBUG | DEMO SOFTWARE-NOT FOR PATIENT USE | HELP | ALARM SILENCE |
|---|---|---|---|
| ↑PATIENT COMPLAINED OF CHEST PAIN AT 3 AM | BED15 RAND JOHNSON ⎡¹ mV ⎣₋₁ 〜〜〜〜〜 ALL ALARMS OFF | | CONT REC<br>HR 87<br>ARR<br>ART 109/75 (98) |
| ↑PATIENT ALLERGY: DEMEROL | BRENDA YOCUM ⎡¹ mV ⎣₋₁ 〜〜〜〜〜 | | CONT REC<br>HR 60<br>ARR<br>LA 12 |
| ↑PATIENT COMPLAINED OF CHEST PAIN AT 3 AM | BED15 RAND JOHNSON ⎡¹ mV ⎣₋₁ 〜〜〜〜〜 | | CONT REC<br>HR 87<br>ARR<br>ART 109/75 (98) |
| ↑PATIENT IN X-RAY | | | CONT REC |
| | BRENDA YOCUM ⎡¹ mV ⎣₋₁ 〜〜〜〜〜 ALL ALARMS OFF | | |
| ↑PATIENT ALLERGY: DEMEROL | BED15 RAND JOHNSON ⎡¹ mV ⎣₋₁ 〜〜〜〜〜 | | CONT REC<br>HR 87<br>ARR<br>ART 109/75 (98) |
| ↑PATIENT COMPLAINED OF CHEST PAIN AT 3 AM | BRENDA YOCUM ⎡¹ mV ⎣₋₁ 〜〜〜〜〜 ALL ALARMS OFF | | CONT REC<br>HR 60<br>ARR<br>LA 12 |
| ↑PATIENT ALLERGY: DEMEROL | | | |

| SC 3000 WORKSTATION | 8x1 NOTES | 23-FEB-96 10:30 |

CENTRAL STATION WAVEFORM DISPLAY HAVING DEDICATED MESSAGE USER AREAS

CROSS-REFERENCE TO RELATED APPLICATION

This is a continuation of Ser. No. 08/618,156 filed Mar. 19, 1996 now abandoned.

BACKGROUND OF THE INVENTION

1. Field of the Invention

The present invention relates generally to methods and apparatus for displaying physiological signals acquired from a patient, and more particularly, to a central station waveform display having dedicated user message areas.

2. Description of the Related Art

In hospitals and other health care environments of the type having a plurality of patient monitors, it is common to have a central review station coupled to receive the physiological signals acquired from a plurality of patient monitors, in order that physiological signals from a plurality of patients can be reviewed or monitored at a single, central location. Such central review stations have been in use for many years, such as those referred to as a "nurses" station or a "workstation" (referred to hereinafter as a central station). From such stations a clinical user can review patient waveforms, vital signs, trend information and other patient data. Central stations also typically remotely annunciate alarms for assigned bedsides, thereby alerting the clinical staff to a potential emergency, and allow remote control of bedside physiological alarm limits and bedside alarm silencing.

FIG. 1 shows how users will typically "post" notes 10 at the display 12 of their central station 14 in order to notify other users of the monitoring system of various important patient conditions and events that they have become aware of, but have not yet been posted or entered into the patient's record or nursing notes, as well as patient location information if the patient is currently disconnected from the central monitoring station. Typically the user will write the information on a piece of paper 10 or surgical tape and stick it to the side of the display 12 or even to the surface of display 12 to insure that anyone who looks at the display will see the note. Unfortunately, such notes 10 can easily become dislodged and fall off, thereby depriving other users of the patient conditions and events that had become known to the prior user.

It would be desirable to provide a patient monitoring system having a central station waveform display that would keep the user message information in a more reliable/secure manner.

Furthermore, it would be desirable that the technique used for securing the message information could be easily implemented with the central review station and in a simple and cost effective manner.

Thus, it is an object of the present invention to provide the user of a central station with a means for reliably securing user messages at the central station, and furthermore for associating the messages with given ones of the patients being monitored.

SUMMARY OF THE INVENTION

A method and apparatus for displaying physiological signals acquired from a patient, comprising the steps of: receiving at a central station physiological signals acquired from a patient; and arranging a display portion of the central station to have at least one first display area dedicated for displaying said physiological signals, and at least one second display area, located adjacent said first display area, dedicated for displaying a user generated message related to the physiological signals displayed in said first display area.

BRIEF DESCRIPTION OF THE DRAWINGS

FIG. 1, previously described, illustrates the display portion of a central station which has user messages posted thereon in accordance with the teachings of the prior art;

FIG. 5 illustrates a further view of the display of a central station constructed and operating in accordance with the present invention.

DETAILED DESCRIPTION OF THE EXEMPLARY EMBODIMENT

Figure 2:
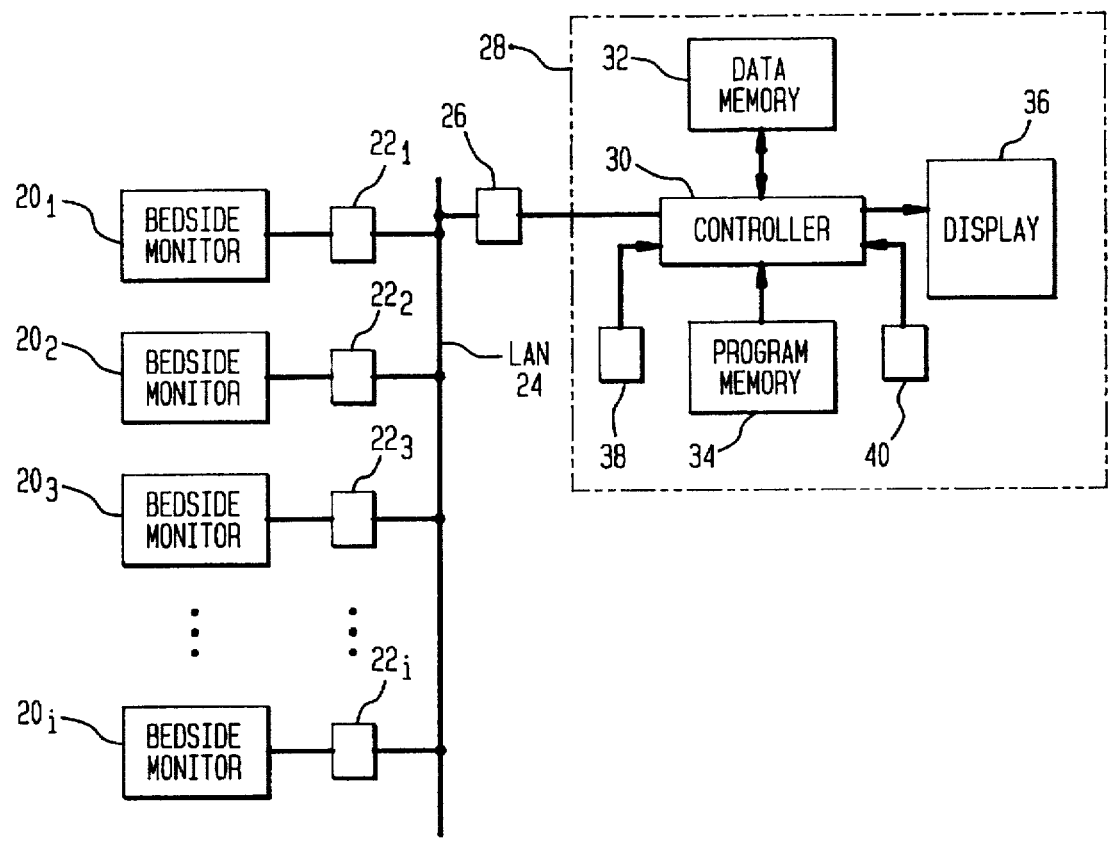
FIG. 2 illustrates in block diagram form a patient monitor system having networked bedside monitors and a central station.
Figure 3:
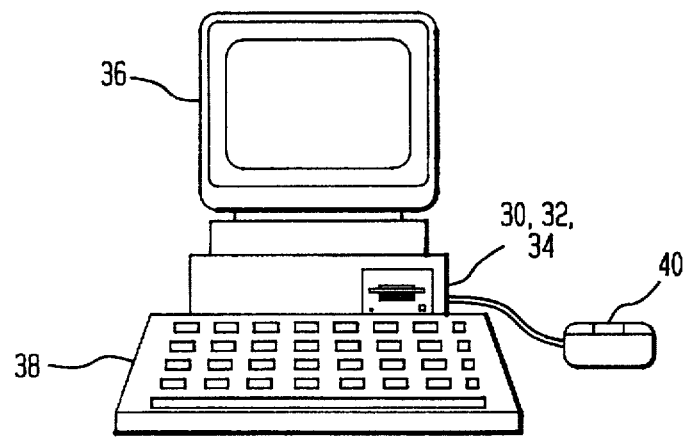
FIG. 3 illustrates an isometric view of the central station shown in FIG. 2.

FIG. 2 illustrates in block diagram form a patient monitor system having a plurality of bedside monitors $20_1$, $20_2$, $20_3$, to $20_i$ which acquire physiological signals from a similar plurality of patients, not shown. As well known, bedside monitors $20_1$, $20_2$, $20_3$, to $20_i$ both display the acquired physiological signals, or a processed version thereof, as well as transmit the acquired signals to a network or LAN 24 via a corresponding plurality of network interface devices, $22_1$, $22_2$, $22_3$, to $22_i$. Also connected to LAN 24 is a further network interface device, $26_1$, for coupling a central station 28 to LAN 24 so that it can also receive the physiological signals. Central station 28 includes a controller 30 which operates in conjunction with a data memory 32 which stores the physiological signals, and under the control of a program (or programs) stored in memory 34, for generating predetermined dedicated areas on a display 36 of central station 28 for display of monitored patient data representative of the received physiological signals. For example, controller 30 may develop on display 36 dedicated areas for display of a duration of the patient EKG waveform, blood pressure or other vital sign trend information. User input devices, such as a mouse 40 and a keyboard 38, are also connected to controller 30 for enabling the user to set-up and operate the central station, as well known to those of ordinary skill in this art.

Figure 4:
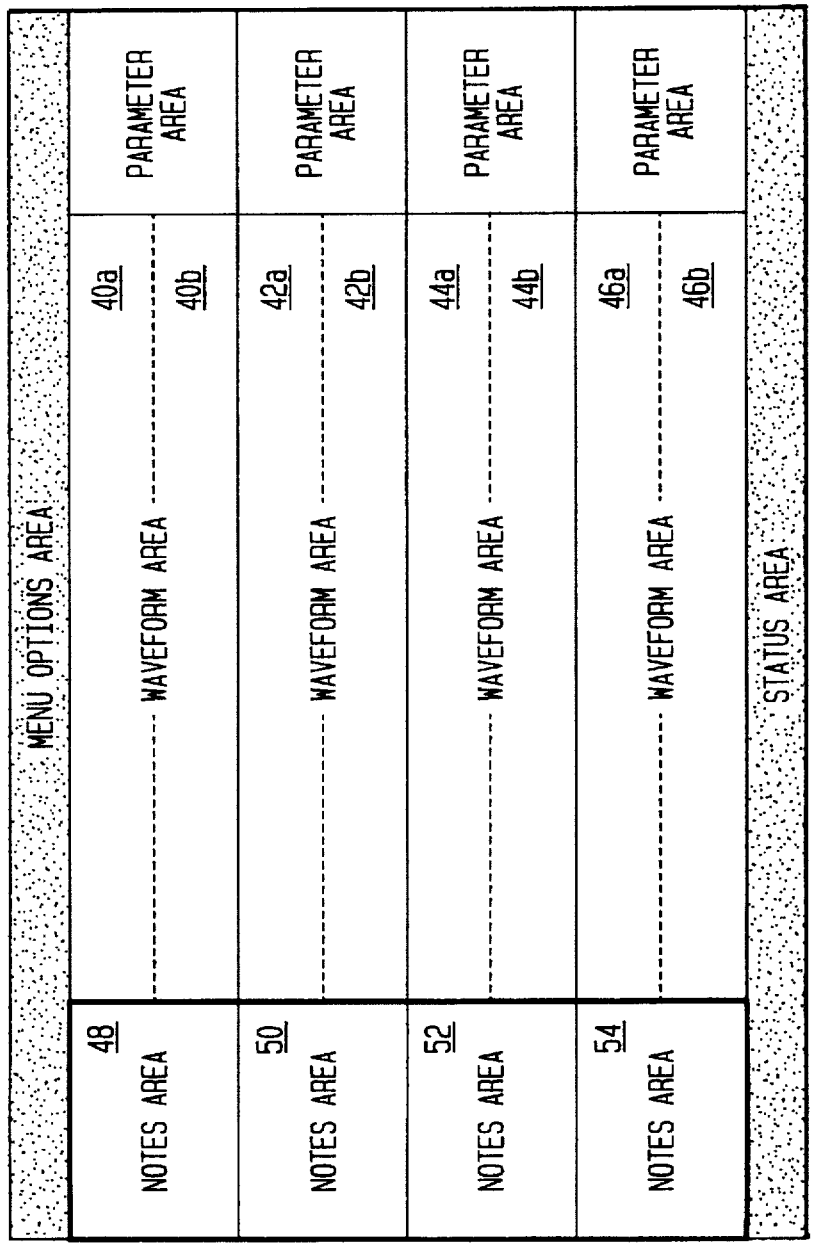
FIG. 4 illustrates the display of a central station constructed and operating in accordance with the present invention.

In accordance with the principles of the invention, the user can also use one or both of input devices 38 and 40 to set up additional dedicated display areas for user messages related to the patients being monitored. FIG. 4 illustrates a central station display screen 36, set-up in accordance with the invention, where there are dedicated "waveform areas" 40, 42, 44 and 46, for the display of patient waveforms, and "notes areas" 48, 50, 52 and 54, for the display of user entered messages or notes related to the patient whose waveforms are displayed in areas 40, 42, 44 and 46, respectively. In the FIG. 4 embodiment, waveform areas 40–46 are each divided along their horizontal dimension into two sections, "a" and "b", each for display of one of two waveforms for each patient. However, the message areas 48–54 are each the height of the combined "a" and "b" waveform areas, since their information content relates to the patient, and not an individual physiological waveform.

In accordance with a further aspect of the invention, the message areas are located on display 36 adjacent to the position of the waveform areas, thereby locating the message information in close proximity to the waveform information of the patient.

More specifically, the present invention is for clinical users who wish to setup electronic message exchange areas on the main screen display of their central station. The display of a message area is selected at the time of main screen configuration programming, i.e., in a Setup Central Layouts screen, as well known by those of ordinary skill in this technology.

As well known, the main screen of the central station displays information for multiple patients simultaneously. The screen is set-up so as to be divided into multiple channels, which, in a preferred embodiment combines to form six different display configurations from which the user can select to display patient data. These configurations, are defined as follows:

A: 16 patients, 1 waveform each (16×1)
B: 8 patients, 1 waveform each (8×1)
C: 8 patients, 2 waveforms each (8×2)
D: 4 patients, 2 waveforms each (4×2)
E: 4 patients, 4 waveforms each (4×4)
F: 2 patients, 4 waveforms each (2×4)

The 16×1, 8×2, and 4×4 configurations are displayed in "split screen" mode, meaning that the screen is split in half vertically with patient data displayed in two columns. Half of the patients are displayed on the left side of the screen and the other half are displayed on the right side of the screen. In split screen mode, four seconds of waveform data is displayed for each patient. The 8×1, 4×2, and 2×4 configurations are displayed in "full screen" mode, meaning patient data is displayed across the entire width of the screen, with ten seconds of waveform data displayed for each patient.

Due to screen size limitations, the message area can only be selected for display with the 8×1, 4×2 and 2×4 layout configurations (full screen configurations). It cannot be selected for display with the 16×1, 8×2 and 4×4 layout configurations (split screen configurations).

The system of the present invention is advantageous over current techniques in that there is no danger of the notes or message "falling" off of the display screen after a period of time, or when someone walks by the nurse's station.

If selected for display, the message areas 48–50 are displayed on the left side of the screen, as shown in FIG. 4, adjacent to their corresponding patient waveform areas 40–46. When the message area is displayed, only eight seconds of waveform are displayed for each patient. The message area is divided so there is a dedicated area for entering notes for each patient data being displayed. The capacity of each patient message area is 256 characters or 20 lines of text, whichever comes first. When the displayed capacity is exceeded, a scroll bar is displayed, indicating that more information has been entered, which allows the user to view all of the notes information.

The specific number of patient message areas displayed is dependent on the specific layout configuration chosen. The size of the message area displayed for each patient is proportional to the vertical height of the waveform area displayed. For example, in an 8×1 configuration, shown in FIG. 5, message areas for eight patients are displayed, and the message area is one waveform channel in height since only one channel of waveform is displayed for each patient. In a 4×2 configuration, such as shown in FIG. 4, message areas for four patients are displayed, and the message area is two channels in height since two channels of waveform are displayed for each patient. Similarly, in a 2×4 configuration, not shown, message areas for two patients would be displayed, each four channels in height.

Figure 1:
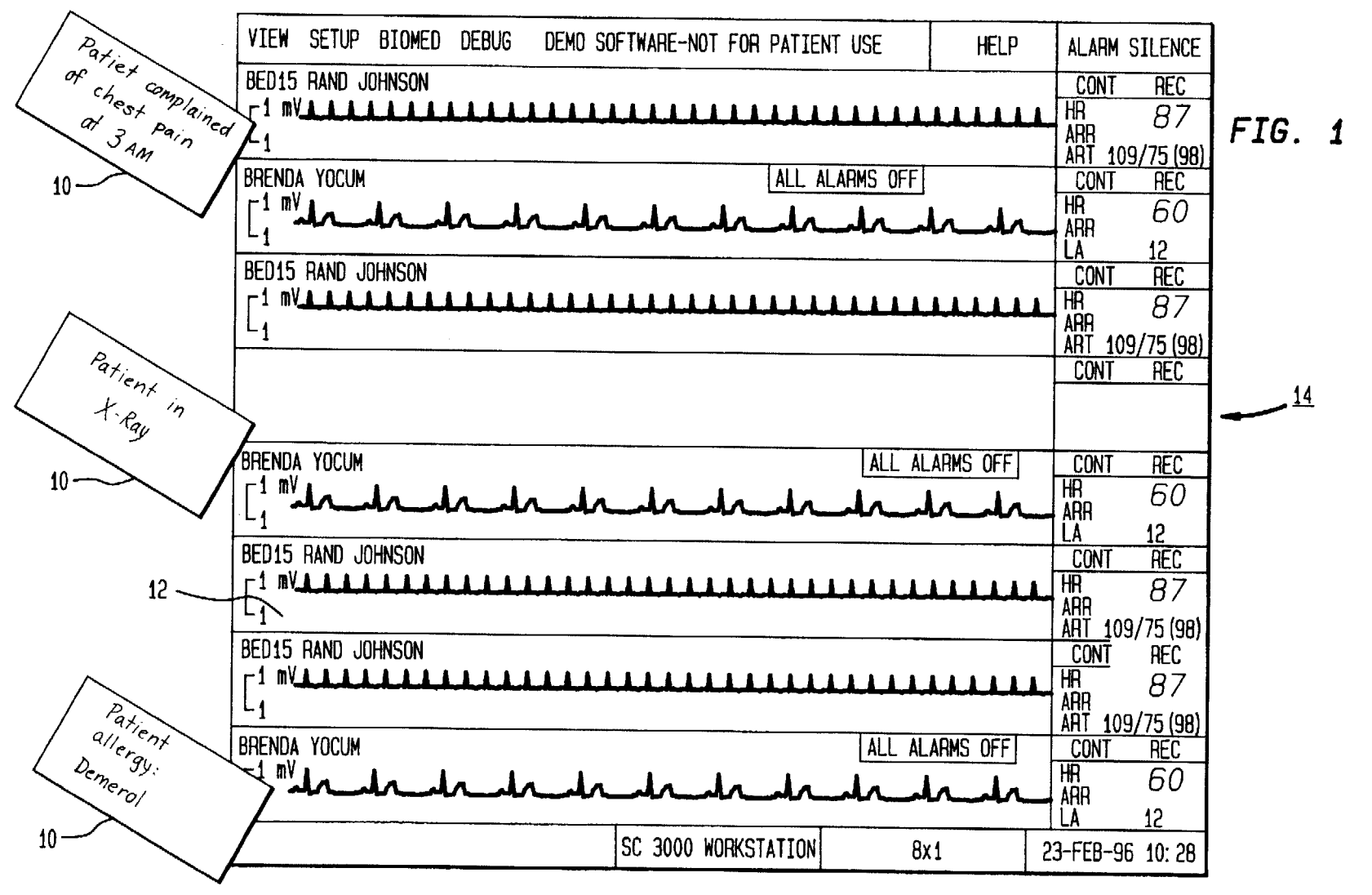

Whenever a message area is displayed in the main screen of the central station, users can enter electronic messages for any patient displayed. Text for the messages are entered via the device keyboard 38, shown in FIGS. 1 and 2.

To begin entering messages for a patient, the user clicks the mouse input device 40 when the navigational pointer (cursor) is over the appropriate message area, or simply moves the pointer over to that message area, and begins typing. When the pointer is moved out of the message area, text entry is not possible. Editing the information is as simple as entering it.

Information displayed in the message area is deleted upon patient discharge or admittance/monitoring of a new patient at that network location. Selecting a new central layout configuration for display does not delete the patient messages.

Thus, what has been shown and described is a new method and apparatus for displaying physiological signals acquired from a patient in a manner that allows for reliably associating user generated message information with the physiological signals acquired from the patient. While a specific embodiment of the present invention has been illustrated and described herein, its is to be realized that modifications and changes will occur to those skilled in the art. For example, the message areas can be used for display of other types of patient information, e.g., trends, events, and lab results. It is therefore to be understood that the appended claims are intended to cover all such modifications and changes as they fall with the true spirit and scope of the invention.

What we claim is:

1. A method for displaying in substantially real-time at a central location physiological signals contemporaneously acquired from a plurality of remotely located patients, comprising the steps of:

receiving at a central station physiological signals acquired in substantially real-time from said plurality of patients; and arranging a display portion of the central station to have a plurality of first and second separate display areas, with a given one of each of said first and said second display areas being arranged on said display so as to be adjacent one another, simultaneously displayed, and used for display of information related to a selected one of said plurality of patients, wherein said first display areas are dedicated for displaying in substantially real-time said physiological signals contemporaneously acquired from said selected patient, and said second display areas are dedicated for displaying messages generated by a user of said central station, said messages being related to the patient whose physiological signals are displayed in said first display areas.

2. The method of claim 1, wherein said arranging step comprises operation by said user of a user input device coupled to said central station for inputting said message to said second display area.

3. The method of claim 2, wherein said arranging step includes the further step of said user operating a mouse input device to select a second display area for message entry, and operating an alpha-numeric keyboard input device for inputting a message into said selected second display area.

4. The method of claim 2, wherein said arranging step includes the further step of said user operating said user input device to cause said display portion to display a plurality of first display areas for a given patient, and a single second display area adjacent said plurality of said first display areas, for said given patient.

5. The method of claim 4, wherein said user operating step includes said user operating said user input device to display a plurality of second display areas, one for each of a plurality of patients.

6. Apparatus for displaying in substantially real-time at a central location physiological signals contemporaneously acquired from a plurality of remotely located patients, comprising:

a plurality of patient monitor means, at least one associated with each of said plurality of patients, each monitor means developing at least one physiological signal representative of a physiological condition of its associated patient;

communication network means, coupled to each of said plurality of patient monitor means, for receiving and transmitting said at least one physiological signal from each of said patient monitor means; and a central display means, coupled to said communication network means and responsive to said physiological signals transmitted thereby, for displaying said physiological signals, said central display means having a plurality of first and second separate display areas simultaneously displayed thereon, with a given one of each of said first and said second display areas being arranged on said display so as to be adjacent one another and used for display of information related to a selected one of said plurality of patients, and wherein said first display areas are dedicated for displaying in substantially real-time said physiological signal contemporaneously acquired from selected ones of said patients, and said second display areas are dedicated for displaying messages generated by a user of said central station, said messages being related to the patient whose physiological signal is displayed in said first display area adjacent thereto.

7. Apparatus according to claim 6, wherein said central display means comprises a central monitor station, including a display, a display controller, and a user input device.

8. Apparatus according to claim 7, wherein said user input device is coupled to said controller and is operable by a user for causing said display to have a plurality of first display areas for each of said patients, and a single second display area located adjacent said plurality of first display areas, for each of said patients.

9. Apparatus according to claim 8, wherein said user input device includes an alpha-numeric keyboard for use by said user for inputting a message into said second display area.

* * * * *